United States Patent [19]

Werner

[11] 4,154,088
[45] May 15, 1979

[54] APPARATUS FOR MEASURING THE PARTICULATE MATTER CONTENT OF A GAS

[75] Inventor: Gert Werner, Copenhagen-Valby, Denmark

[73] Assignee: F. L. Smidth & Co., Cresskill, N.J.

[21] Appl. No.: 657,183

[22] Filed: Feb. 11, 1976

[30] Foreign Application Priority Data

Feb. 12, 1975 [GB] United Kingdom ............... 5970/75

[51] Int. Cl.² .................................................. G01N 31/00
[52] U.S. Cl. .................................. 73/28; 73/421.5 A
[58] Field of Search ........ 73/28, 23, 432 PS, 421.5 A, 73/421.5 R; 55/267, 270

[56] References Cited

U.S. PATENT DOCUMENTS

| | | | |
|---|---|---|---|
| 1,100,171 | 6/1914 | Brown | 73/28 |
| 2,987,921 | 6/1961 | Kraftson | 73/421.5 A |
| 3,478,600 | 11/1969 | Lynn | 73/28 |
| 3,495,463 | 2/1970 | Howell | 73/421.5 A |
| 3,759,087 | 9/1973 | Inao et al. | 73/23 |
| 3,784,902 | 1/1974 | Huber | 73/28 |

FOREIGN PATENT DOCUMENTS 1815045  6/1970  Fed. Rep. of Germany ..... 73/421.5 A

*Primary Examiner*—Stephen A. Kreitman
*Attorney, Agent, or Firm*—Pennie & Edmonds

[57] ABSTRACT

Apparatus for measuring the particulate content of a gaseous medium includes temperature control devices for permitting application to both hot gases and cold, wet gases. Specifically, the apparatus comprises an exhaust nozzle for coupling with a duct through which gas passes; a filter housing including a filter; an exhaust tube, having a heat exchange passage therein, connected between the nozzle and the filter housing; an exhaust device; a conduit for coupling a heat exchange medium to the exhaust tube passage; and a controllable heating element for heating the heat exchange medium in the conduit between a source and the exhaust tube. In preferred embodiments, the heating element is arranged around the filter housing in heat exchange relationship with the conduit, providing temperature conditioning of both the medium and the filter housing in a very compact apparatus. In a specific example of this embodiment, the heating means and the conduit are arranged in interlaced helices about the filter housing. In further preferred embodiments, the heating means is controlled by a gas temperature sensing element disposed in the exhaust gas path. Such an arrangement permits automatic control of the gas temperature to a pre-set level.

13 Claims, 8 Drawing Figures

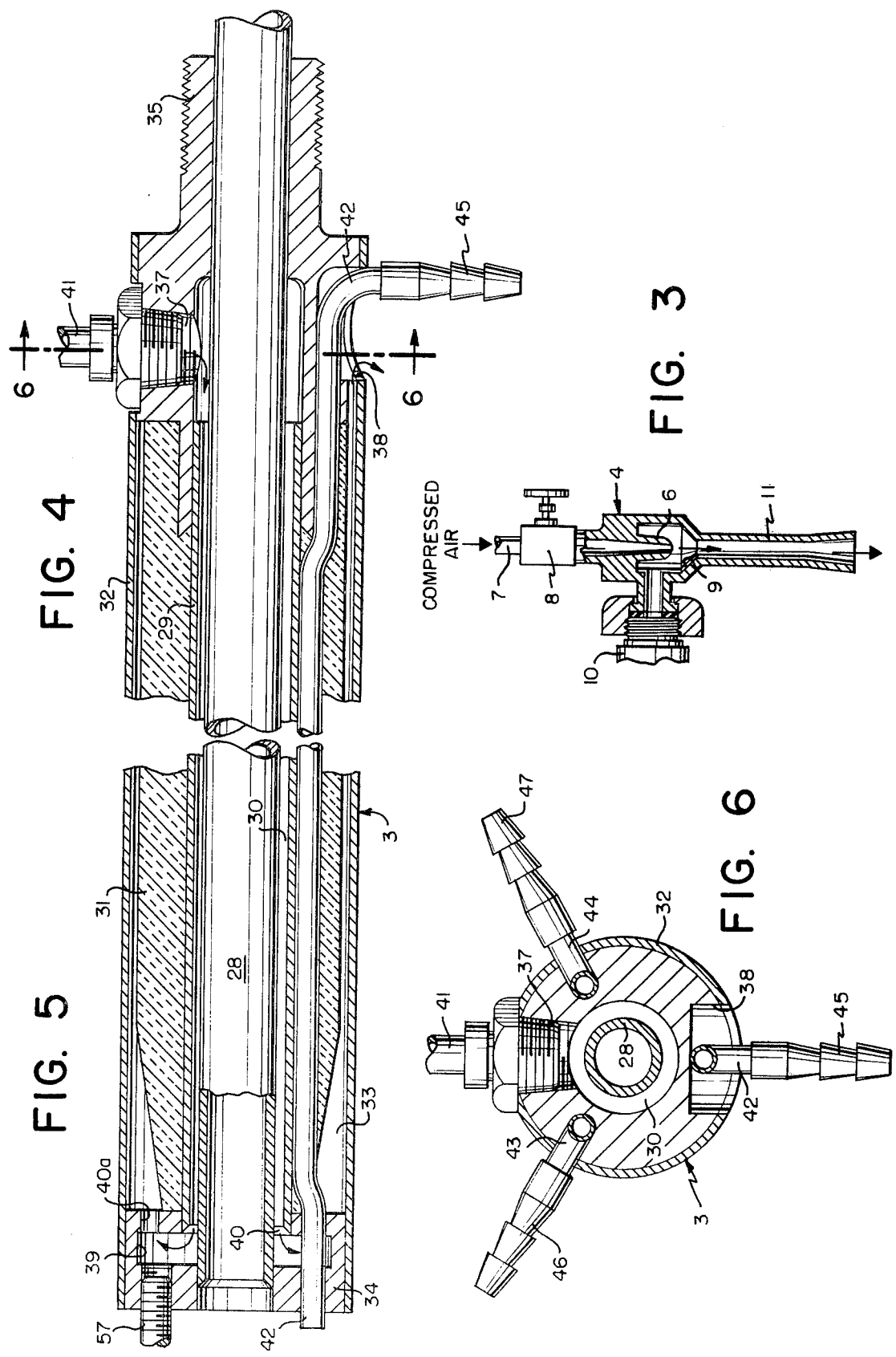

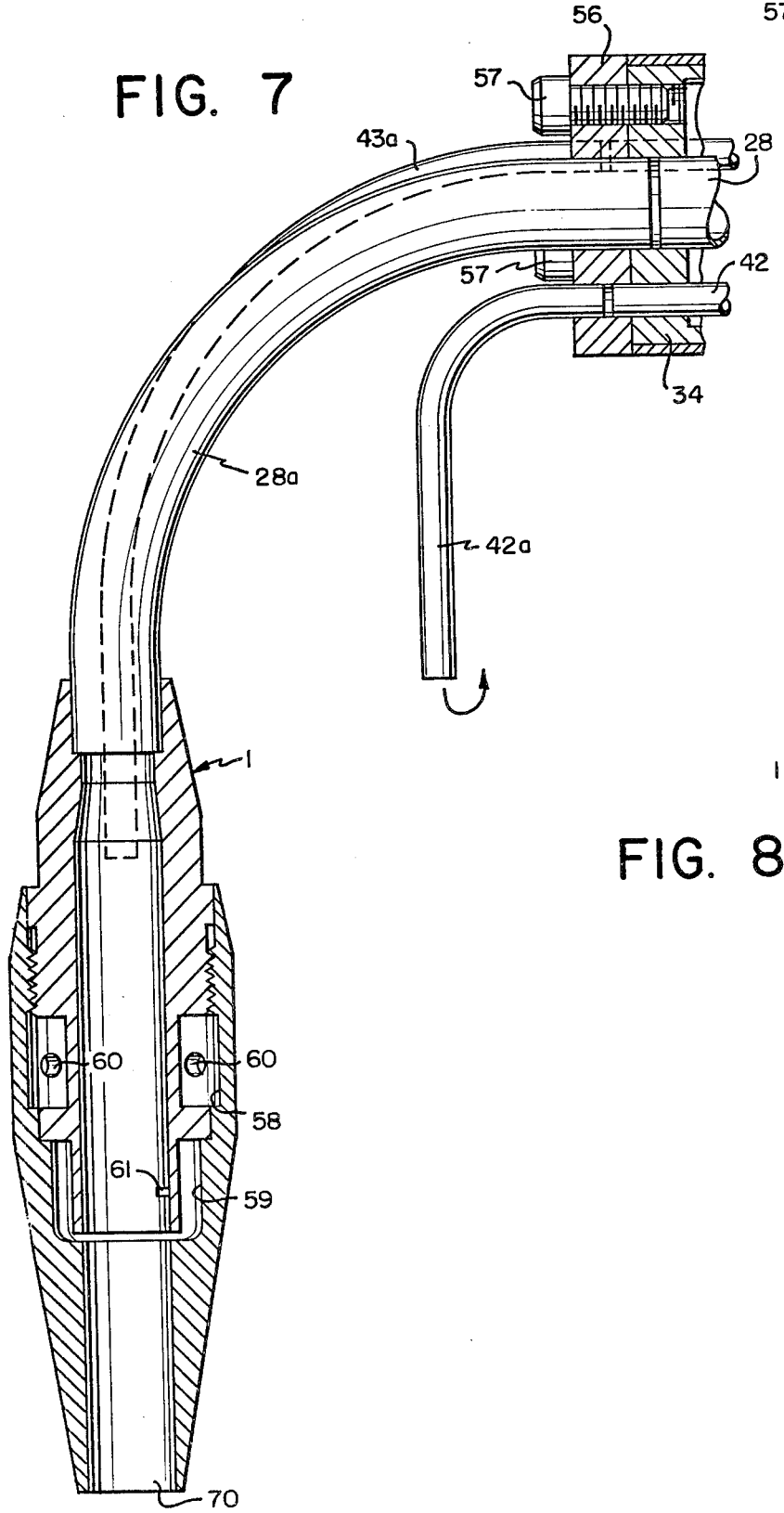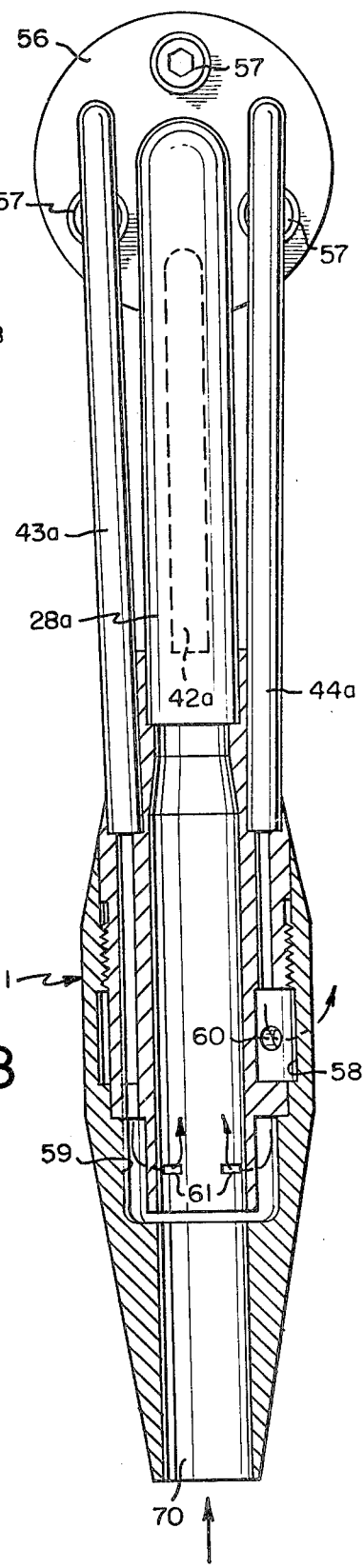

APPARATUS FOR MEASURING THE PARTICULATE MATTER CONTENT OF A GAS

BACKGROUND OF THE INVENTION

1. Field of the Invention

This invention relates to apparatus for measuring the particulate matter content in a gaseous medium; and, more particularly, to such measuring apparatus which includes a temperature control device for permitting application both to hot gases and to cold, wet gases.

2. Description of the Prior Art

Apparatus for measuring the particulate matter content of gaseous media are significant components in many systems for monitoring and controlling particulate emissions. As acceptable levels of such emissions have been progressively lowered, the need for greater accuracy in such measuring apparatus has been accentuated. A typical prior art particulate matter measuring apparatus comprises an exhaust nozzle connected to a filter housing by an exhaust tube, a filter disposed in the housing, and an exhaust device, such as an ejector, connected to the housing. In operation, the nozzle is coupled to a duct through which a gas medium containing particulate matter, e.g., dust, passes and the exhaust device is activated. A portion of the gas medium is drawn through the nozzle, the duct, and the filter and then through the exhaust device, out of the apparatus. Particulate matter is removed from the medium by the filter. Using this apparatus, one can monitor the rate of flow of gas through the duct by measuring the quantity of gas exhausted when the suction of the exhaust device is adjusted to equate the intake velocity of the gas through the nozzle with the velocity of gas through the duct. Under these conditions, one can calculate the total amount of particulate matter carried by the gas in the duct from a measurement of the particulate matter collected by the apparatus filter.

While some devices for high or low temperature applications have been provided with air-cooled exhaust tubes and electrically heated exhaust tubes, respectively, none of the prior art devices provide a compact device suitable for both temperature extremes as well as intermediate levels likely to be encountered in operation. In apparatus for high temperature applications, e.g., for measuring the hot gases exhausted by a rotary kiln, it is necessary to prevent excessive heating of the filter. In such applications, it is known to use an air-cooled exhaust tube which is typically an exhaust tube with a jacket having passages for receiving compressed air. The compressed air cools the exhaust tube and, thereby, the hot gases therein.

In apparatus for low temperature applications, e.g., for measuring cold, wet gases, it is necessary to prevent undue condensation in the apparatus, for the condensate can trap dust before it reaches the filter and thereby interfere with accurate measurement. In such applications, it is known to use an electrically heated exhaust tube which is typically an exhaust tube provided with a jacket containing electrical heating elements.

While exhaust tubes cooled by compressed air have proved to be satisfactory when the content of dust in hot gases is to be measured, and electrically heated exhaust tubes have proved to be satisfactory when the content of dust in cold, wet gases is to be measured, it is often impractical to shift between the two different types of exhaust tubes when different conditions are encountered.

SUMMARY OF THE INVENTION

In accordance with the invention, apparatus for measuring the particulate content in a gaseous medium includes temperature control devices for permitting application to both hot gases and cold, wet gases. Specifically, the apparatus comprises an exhaust nozzle for coupling with a duct through which gas passes; a filter housing, including a filter; an exhaust tube, having a heat exchange passage therein, connected between the nozzle and the filter housing; an exhaust device; a conduit for coupling a heat exchange medium to the exhaust tube passage and a controllable heating element for heating the heat exchange medium in the conduit between a source and the exhaust tube. In preferred embodiments, the heating element is arranged around the filter housing in heat exchange relationship with the conduit, providing temperature conditioning of both the medium and filter housing in a very compact apparatus. In a specific example of this embodiment, the heating means and the conduit are arranged in interlaced helices about the filter housing. In further preferred embodiments, the heating means is controlled by a gas temperature sensing element disposed in the exhaust gas path. Such an arrangement permits automatic control of the gas temperature to a pre-set level.

BRIEF DESCRIPTION OF THE DRAWING

The advantages, nature, and various features of the prevent invention will appear more fully upon consideration of the illustrative embodiments now to be described in detail in connection with the accompanying drawing.

In the drawing:

FIG. 3 shows an axial section of an exhaust device for the apparatus shown in FIG. 1, FIGS. 4 and 5 show longitudinal sections of the rear and front end, respectively, of an exhaust tube construction for the apparatus in FIG. 1, FIG. 6 shows a cross section of the exhaust tube construction along section line 6—6 in FIG. 4, and FIGS. 7 and 8 show a side view section and a front view section, respectively, of a nozzle for the apparatus shown in FIG. 1.

For convenience of reference, identical elements will be designated by the same reference numeral throughout the drawing.

DETAILED DESCRIPTION OF THE DRAWING

Figure 1:
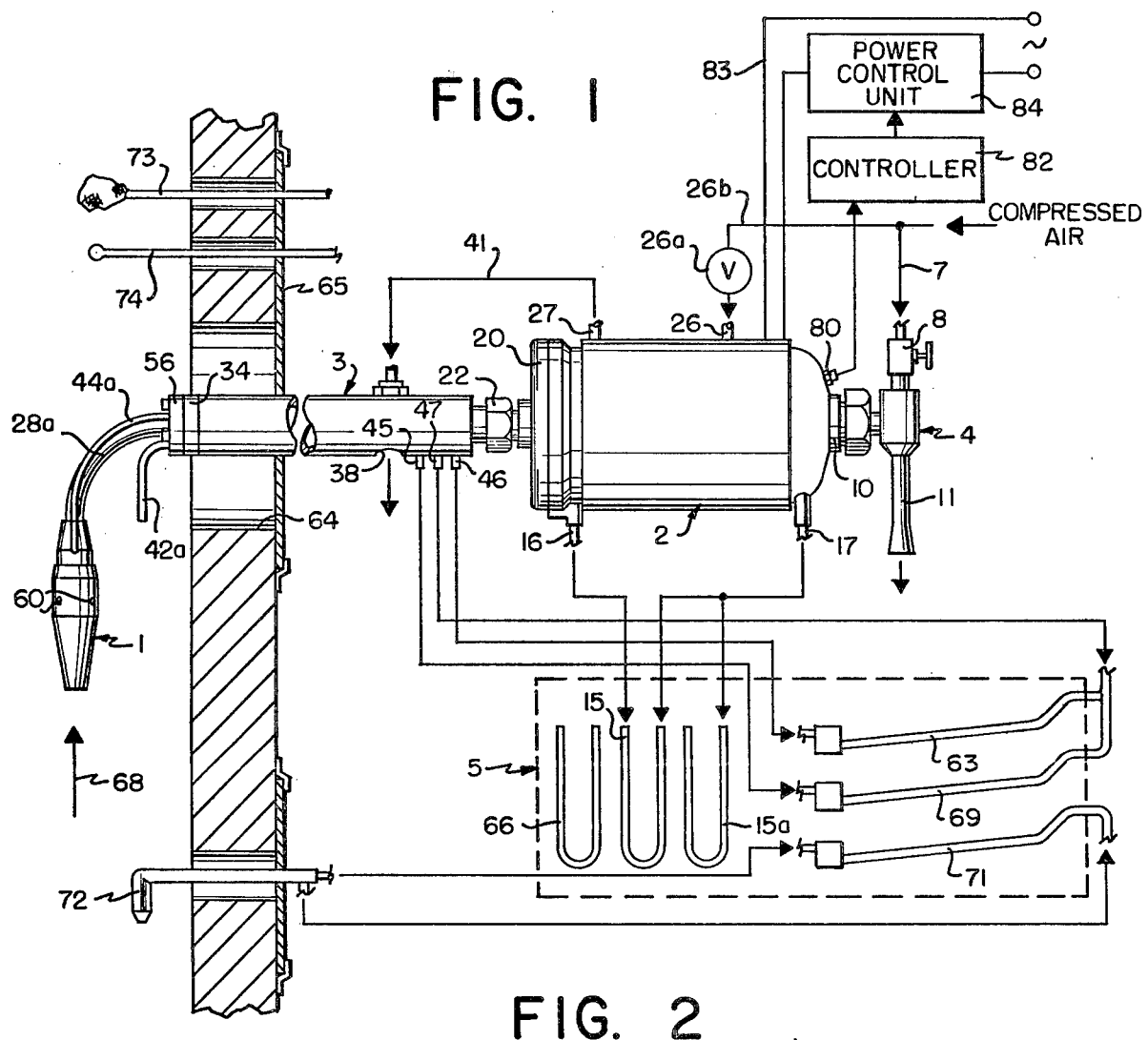
FIG. 1 is a diagrammatic side view of a preferred embodiment of the apparatus according to the invention.

Referring to the drawing, FIG. 1 illustrates a preferred embodiment of apparatus for measuring the particulate matter content of a gaseous medium passing through a duct. The apparatus comprises an exhaust nozzle 1 for pneumatically coupling the apparatus with the duct, a filter housing 2 including a filter for the particulate matter (element 13 of FIG. 2); and an exhaust tube construction 3 connecting the nozzle and the filter housing. An exhaust device 4 is connected to the filter housing for drawing the gaseous medium 68 from the duct, through the nozzle, exhaust tube, and a filter and ejecting it from the apparatus.

The exhaust tube construction 3 is provided with a heat exchange passage (element 30 of FIGS. 4, 5, and 6)

for receiving a heat exchange medium, such as air, from a source (not shown). A controllable heating element (element 23a of FIG. 2) is provided for heating the medium prior to its arrival to passage 30.

In the embodiment of FIG. 1, the nozzle 1 is disposed in the duct through which gas 68 flows. The front end of the exhaust tube construction 3 extends through a hole 64 in the wall of the duct, and the hole is closed by means of a cover plate 65.

A specific embodiment of an exhaust nozzle preferred for use in this apparatus is illustrated in FIGS. 7 and 8. In the nozzle illustrated, known as a balanced nozzle, the interior of the nozzle is by means of tube 28a connected to a flange 56. Two tubes 43a and 44a further connect the nozzle with the flange. The flange 56 is by screws 57 connected to the front end mounting 34 of the exhaust tube construction, illustrated in FIG. 7, in such a way that communication exists between the tube 28a and the inner tube 28, as illustrated in FIG. 7, between the tube 43a, shown in FIG. 8, and the transfer tube 43, shown in FIG. 6, and between the tube 44a, also shown in FIG. 8, and the transfer tube 44, shown in FIG. 6. Moreover, a small tube 42a is secured to the flange 56 so as to communicate with the transfer tube 42 in the exhaust construction, as illustrated in FIG. 7.

The nozzle itself contains two chambers 58 and 59. The chamber 58 is in connection with the tube 44a, shown in FIG. 8, and communicates with the outer surface of the nozzle through radially extending holes 60, also shown in FIG. 8, which accordingly communicate the static pressure prevailing outside the nozzle to the hose connector 47, illustrated in FIG. 6.

The chamber 59 is in connection with the tube 43 and communicates through radially inwardly directed holes 61 with the interior of the nozzle, as illustrated in FIG. 8, and accordingly the static pressure prevailing at the interior of the nozzle is communicated via the tube 43a and the tube 43, shown in FIG. 6, to the hose connector 46.

Figure 2:
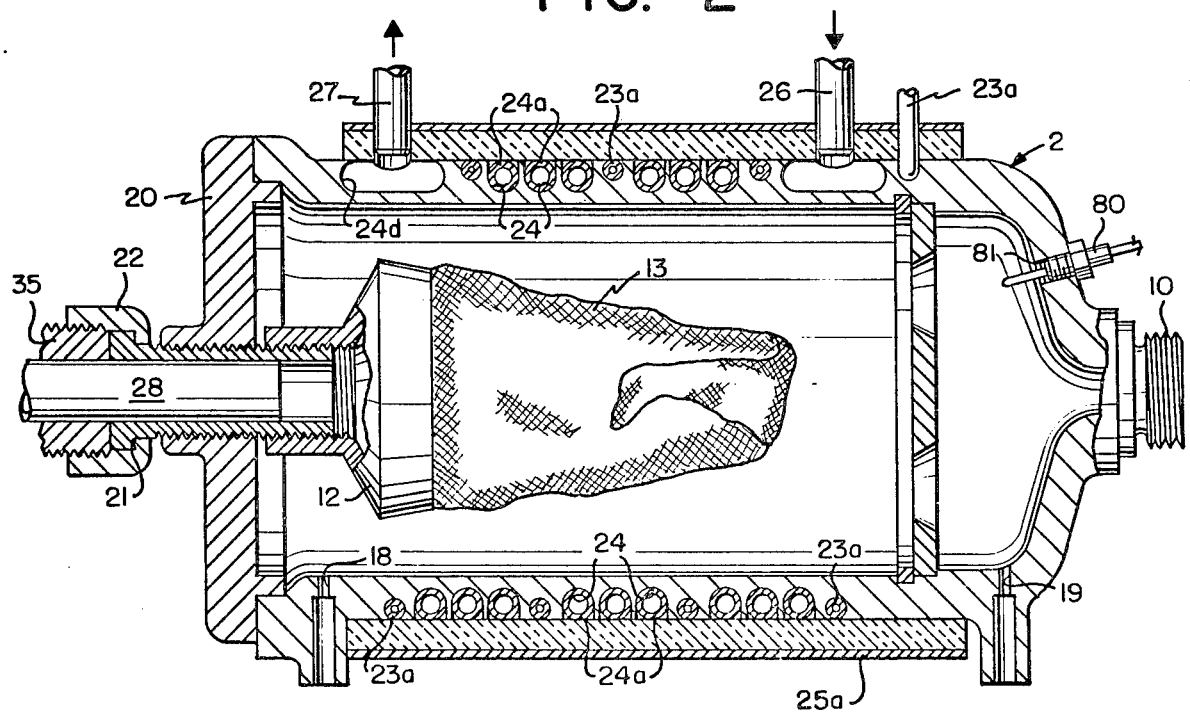
FIG. 2 shows an axial section of a filter housing forming a part of the apparatus shown in FIG. 1.

A specific embodiment of filter housing 2 is illustrated in FIG. 2. The housing of FIG. 2 contains a socket 12 to which a filter bag 13 is secured. The front or inlet end of the housing is closed by means of a cover 20, having a central hole wherein a threaded pipe stub 21 is secured. Socket 12 is, by means of threading, secured to the rear end of stub 21, while the front end of stub 21 serves as a connection to the exhaust tube construction 3 by means of a pipe union (element 22 of FIG. 1). As is well-known in the art, the selection of the particular filter used depends upon the type and size of the particulate matter to be collected. An alternative to the use of filter bag 13 is the use of one or more filter cups. Such alternative use merely requires the use of another socket (not shown) adapted for such cups.

A specific embodiment of an exhaust tube construction is illustrated in FIGS. 4, 5, and 6. The construction there shown comprises an inner exhaust tube 28 and an intermediate tube 29 surrounding the inner tube 28 coaxially so as to form an air passage 30 therebetween. The intermediate tube 29 is preferably surrounded by a layer of heat insulating material 31 which coaxially is surrounded by an outer tube 32 so as to form an outer air passage 33 between the outer surface of the insulating material 31 and the inner surface of the outer tube 32. The tubes 28, 29, and 32 are at each end secured to an end mounting, viz., a front end mounting 34, illustrated in FIG. 5, and a rear end mounting 35, illustrated in FIG. 4. The rear end mounting 35 is adapted to be secured to the stub 21 by means of the union 22 so as to secure communication between the inner tube 28 and the socket 12. Moreover, an air inlet 37 is provided in the rear mounting 35 for admitting compressed air to the air passage 30 formed between the inner tube 28 and the intermediate tube 29. Further, an air outlet 38 is provided at this end of the exhaust tube construction. The outlet 38 connects the outer air passage 33 with the atmosphere. At the front end of the exhaust tube construction, illustrated in FIG. 5, the front mounting 34 allows the air which reaches the front end via the duct 30, to return via the outer air passage 33.

The air reaching the front end mounting via the duct 30 flows through a central opening 40, wherein the front end of intermediate tube 29 is secured, into a chamber 39 and from chamber 39 through holes 40a, illustrated in FIG. 5, into the outer air passage 33.

The inlet 37 is connected with the outlet 27 from the air tubes 24a surrounding the filter housing 2 by means of a connecting tube 41, as illustrated in FIG. 1. Three pressure transfer tubes 42, 43, and 44, illustrated in FIG. 6, extend along the intermediate tube 29, embedded in the insulating material 31. In FIGS. 4 and 5, only one of the tubes, namely, 42, is illustrated. At the rear end mounting, illustrated in FIG. 4, the ends of the tubes 42, 43, and 44 are secured to hose connectors 45, 56, and 47, respectively, as illustrated in FIG. 6. The front ends of the pressure transfer tubes are secured in the mounting 34, as illustrated in FIG. 5.

A specific embodiment of an exhaust device 4 is illustrated in FIG. 3. The device comprises an ejector nozzle 6 which, by means of conduit 7, can be fed compressed air from a compressor (not shown). The flow rate through the nozzle 6 can be adjusted by means of a control valve 8. The nozzle 6 opens into an expansion chamber 9 which is in communication with the interior of the filter housing 2 via a connector collar 10. The effluent from the chamber 9, specifically, the air ejected through the nozzle 6 and gases exhausted from the filter housing 2 escape to the atmosphere via an outlet 11.

A specific embodiment of a controllable heating element is illustrated in conjunction with the filter housing in FIG. 2. In this embodiment, the heat exchange medium is coupled from its source to the exhaust tube heat exchange passage by tubes 24a, such as an air tube. The controllable heating element is preferably in the form of an electrical heating wire 23a. The heating element 23a and the tube 24a are thermally coupled together and to the filter housing by spacing these respective components in close adjacency, making the housing of thermally conducting material and disposing a thermal insulating material 25, which can be enclosed by metal jacket 25a, around the outside portion of said components away from the filter.

In the preferred arrangement, both the heating wire 23a and the tube 24a are in the form of helices arranged around the filter housing. To promote thermal coupling between them, the helices are advantageously interlaced and of substantially equal radii. To promote thermal coupling with the filter housing and thence with the filter, the helices are arranged around the filter housing, preferably in contact with a thermally conductive portion thereof. Conveniently, as shown in FIG. 2, these helical components are disposed in grooves in the filter housing wall. Specifically, along the circumference of the housing 2, helical grooves 23 and 24 are provided for accommodating electric heating wires 23a and air tubes 24a. In this specific embodiment a single groove 23 for the heating wire 23a extends in a single helical path from one end of the housing to the other. Three helical grooves 24 are provided for air tubes 24a. As illustrated in FIG. 2, the groove 23 is interlaced with the set of three air tube grooves 24a; and, accordingly, the helices of the air tubes and the heating wires are also interlaced. The three air tubes 24a are mutually connected at both ends of the housing by manifolds 24b and 24d and merge by means of the manifolds into an inlet 26 at one end of the housing and into an outlet 27 at the other end of the housing 20 as to conduct air along three parallel helical paths from one end of the housing to the other. As shown in FIG. 1, the inlet 26 is by means of a control valve 26a connected to a conduit 26b which is branched off from the conduit 7 in such manner so as to admit compressed air to the air tubes 24a from a source, such as a compressor (not shown).

In the preferred embodiment of FIG. 1, the controllable heating element is automatically controlled to control the gas temperature to a pre-set temperature at the filter housing. As illustrated in FIG. 1, a temperature sensing device 80, e.g., a thermocouple or resistant thermometer is arranged in the exhaust gas path, for example, near the outlet of the filter housing 2. A threaded hole 81 shown in FIG. 2 is used for securing the temperature feeler. The temperature sensing device is connected to a controller 82 as indicated in FIG. 1. The controller 82 is a combined indicating and signaling instrument which shows the difference between the set-point (namely, the temperature aimed at) and the temperature actually measured and which issues an electric signal in proportion to the difference. The output signal from the controller 82 may be used in order to automatically control a circuit 83, illustrated in FIG. 1, which feeds the electric heating means surrounding the filter housing. Such control may be carried out by connecting the controller 82 to a power control unit 84 adapted, e.g., for triac control and connected with the circuit 83.

However, when using the apparatus, an operator may also read the difference indicated by the controller 82 between the set-point and the temperature actually measured and use this reading as a guidance for adjusting the electric heating, e.g., by means of a manually operated rheostat. Moreover, it should be understood that the temperature control may also be carried out by adjusting the valve 26a which controls the amount of compressed air fed to the air tubes 24a, surrounding the filter housing 2. By means of this control the amount of air which via the conduit 41 is circulated through the exhaust tube construction via the passages 30 and 33 can also be controlled. Such control may be carried out either manually or by controlling the valve 26a automatically, e.g., via the output signals from the controller 82. When cooling is required in order to avoid excessive heating of the filter 13, illustrated in FIG. 2, the electric heating, of course, is not used. Instead the amount of cooling air is adjusted by means of the valve 26a in order to keep the temperature at the outlet end of the filter housing 2 at a pre-set temperature which is well below the temperatures detrimental to the filter, but also well above the dew point.

As an aid to the operator, a pair of thermometers 73 and 74 may be arranged in the duct as illustrated in FIG. 1, so as to measure the temperature prevailing in the duct. The thermometer 73 is provided with a wet piece of cloth in order to measure the wetbulb temperature so as to calculate the relative humidity of the gas flowing in the duct. This measurement helps the operator in deciding whether the exhaust tube construction 3 should be heated. If the temperature measurements prove that the dew point of the gas is comparatively high, a latent danger exists that condensation will occur during the passage of the gas through the apparatus towards the filter bag, and accordingly heating of the air circulated through the exhaust tube construction should be used. If, on the other hand, the temperature of the gas in the duct is high and the dew point low, this indicates to the operator that the exhaust construction should be cooled. In the first instance, electric heating means are switched on and, in the latter instance, cold compressed air is circulated through the exhaust tube construction 3.

In the preferred embodiment illustrated, the apparatus is provided with an arrangement for automatically controlling the gas velocity in the nozzle to that of the gas in the duct. This control is effected by providing means responsive to any pressure differential between the interior of the nozzle and the duct for adjusting the rate of exhaust of the exhaust device to eliminate such difference. In FIG. 1 two hose connectors 46 and 47 from the two nozzle chambers 58 and 59 (shown in FIGS. 7 and 8) are connected to either end of an inclined tube manometer 63. Accordingly, the manometer 63 shows the difference in static pressure between the outer surface of the nozzle and the interior of the nozzle. Therefore, if the manometer 63 is in level, no such difference exists and the velocity through the nozzle is identical with the velocity outside the nozzle. When the apparatus is in use, the valve 8 is controlled so as to adjust the exhaust effect applied at the outlet end of the filter housing 2. Such adjusting is carried out until the ends of the column in the manometer 63 are in level. When this condition is achieved, the velocities outside and within the nozzle are identical.

The embodiment illustrated preferably also includes an indicator device 69 for indicating the velocity of gas flowing in the duct. The operation of this device may be seen by reference to FIG. 1 wherein the direction of duct gas flow is indicated by means of an arrow 68, and wherein the opening of the small tube 42a is directed opposite this direction of flow. Accordingly, the tube 42a will transmit the total pressure via the transfer tube 42 to the hose connector 45 which, as shown in FIG. 1, is connected to one end of an indicator such as an inclined tube manometer 69 mounted on panel 5. The other end of this tube manometer is connected to the hose connector 47, and therefore the manometer 69 measures the difference between the total pressure and the static pressure, namely, the velocity pressure for the gas flow in the duct. Accordingly, it is possible to calculate the velocity with which the gas passes the nozzle 1 and enters the nozzle. The inlet end 70 of the nozzle has a well-defined area, and the cross-sectional area of the flow duct in the nozzle is constant until the flow has passed the holes 60. By measuring the cross-sectional area of the duct wherein the nozzle is provided, it is, accordingly, possible to calculate the amount of gas passing the duct. Of course, the velocity will not be the same at each point of the cross-sectional area of the duct but when the cross-section form of the duct is known, the velocity profile is also known. Therefore, it is possible to calculate the average velocity or the nozzle 1 may be positioned at a location where the average velocity prevails.

A third inclined tube manometer 71 is connected to a pitot tube 72 which also extends into the gas flow. The manometer 71 is used in order to check the manometer 69. In the event that high velocities occur in the duct, the third U-tube manometer 66 may be used instead of the inclined tube manometer 71 for measuring the pitot pressure.

In addition, the preferred embodiment includes an indicator device for indicating the amount of gas passing through the filter housing. As shown in FIG. 2, between the filter bag 13 and the collar 10 an apertured disc 14 is positioned which combined with one of the U-tube manometers 15 shown in FIG. 1 forms an orifice-meter. Each of the two branches of the U-tube 15 is by means of rubber tubes 16 and 17, respectively, connected to radially extending bores 18 and 19, respectively, which are arranged at either side of the disc 14 in the filter housing. The two bores 18 and 19 are adapted to transfer the static pressures prevailing at either side of the disc to the U-shaped tube 15 which accordingly measures the drop in static pressure over the disc 14. Knowing the aperture constant (c) for the disc and the drop in static pressure over the disc permits the amount of gas passing the filter housing to be easily calculated. As shown in FIG. 1, from the rubber tube 17 a branch 17a leads to one of the branches of another of the U-tube manometers 15a, the other branch of which communciates with the atmosphere. As shown in FIG. 2, the cross-sectional area of the filter housing is several times greater than the cross-sectional area of the exhaust tube construction. This fact combined with the throttling of the gas through the disc 14 has the effect that the gas after having passed the disc has a very small velocity only, and, accordingly, practically no difference exists between the static pressure and the total pressure. As will be explained, the temperature is also measured at the outlet end of the filter housing and accordingly the amount of gas passing the filter housing may easily be re-calculated at standard temperature and pressure.

Although the apparatus according to this invention has been described above with particular reference to air as the medium for conditioning the exhaust tube construction 3 as well as the filter housing 2, it should be understood that the application of the invention is not limited to this particular medium, but that any medium capable of effecting heat transfer may be used instead of air. Moreover, it should be understood that many variations and modifications of the apparatus may be made without departing from the spirit and scope of the invention disclosed and claimed in the following claims.

I claim:

1. An apparatus for measuring the particulate matter content of a gaseous medium passing through a duct comprising:
   an exhaust nozzle for pneumatically coupling said apparatus with said duct;
   a filter housing including a filter for said particulate matter;
   an exhaust tube construction connecting said nozzle and said filter housing, said construction having at least one heat exchange passage therein for receiving a heat exchange medium and thermally coupling said heat exchange medium to said gaseous medium;
   an exhaust device connected to said filter housing for drawing said gaseous medium from said duct through said filter;
   a helical tube arranged about said filter housing for coupling a source of heat exchange medium to said exhaust tube heat exchange passage;
   a helical controllable electrical heating element arranged about said filter housing thermally coupled to the coils of said helical tube;
   temperature sensing means disposed in position for measuring the temperature of said gaseous medium passing through said apparatus; and
   control means for controlling said controllable heating element responsive to said temperature sensing means so as to control the temperature of said heat exchange medium coupled to said exhaust tube heat exchange passage thereby permitting selective heating or cooling of the gaseous medium passing through said filter housing.

2. An apparatus according to claim 1 wherein:
   said helical tube and said helical electrical heating element are interlaced helices.

3. An apparatus according to claim 1 wherein said helical tube and said helical electrical heating element have substantially equal radii.

4. An apparatus according to claim 1 wherein:
   said filter housing is comprised of a thermally conductive material; and
   said helical tube and said helical electrical heating element are disposed in contact with said filter housing.

5. An apparatus according to claim 4 wherein:
   said helical tube and said helical electrical heating element are disposed in contact with the outer surface of said thermally conducting filter housing; and
   a layer of insulating material is arranged around said helical tube and said helical electrical heating element for enhancing the thermal coupling among said tube, said element and said housing.

6. An apparatus according to claim 1 wherein said exhaust nozzle is a balanced nozzle.

7. An apparatus according to claim 1 wherein said exhaust tube construction comprises an inner exhaust tube and a larger diameter intermediate tube surrounding said inner exhaust tube in such a manner as to form said heat exchange passage between the respective tubes.

8. An apparatus according to claim 1 wherein:
   said exhaust device comprises an ejector nozzle for introducing pressurized gas into an expansion chamber; and 9. An apparatus according to claim 1 wherein said apparatus includes means for automatically controlling the gas velocity in said nozzle to the level of gas velocity in said duct.

10. An apparatus according to claim 1 wherein:
    pressure sensing means are disposed in position for measuring the difference in pressure between the interior of said exhaust nozzle and the interior of said duct; and
    said exhaust device is provided with control means responsive to said pressure sensing means for controlling the rate of exhaust of the exhaust device and thereby equalizing the pressure in the interior of said nozzle with the pressure in the duct.

11. An apparatus according to claim 1 wherein said apparatus includes indicator means for indicating the velocity of gas flowing in the duct.

12. An apparatus according to claim 1 wherein said apparatus includes indicator means for indicating the amount of gas passing through the filter housing.

13. An apparatus for measuring the particulate matter content of a gaseous medium passing through a duct comprising:

- an exhaust nozzle for pneumatically coupling said apparatus with said duct;
- a filter housing including a filter for said particulate matter;
- an exhaust tube construction connecting said nozzle and said filter housing, said construction having at least one heat exchange passage therein for receiving a heat exchange medium and thermally coupling said heat exchange medium to said gaseous medium;
- an exhaust device connected to said filter housing for drawing said gaseous medium from said duct through said filter;
- a helical tube arranged about said filter housing for coupling a source of heat exchange medium to said exhaust tube heat exchange passage;
- a helical controllable electrical heating element arranged about said filter housing thermally coupled to the coils of said helical tube;
- temperature sensing means disposed in position for measuring the temperature of said gaseous medium passing through said apparatus;
- means for controlling the flow rate of the gaseous medium through said filter; and
- control means for controlling said controllable heating element responsive to said temperature sensing means so as to control the temperature of said heat exchange medium coupled to said exhaust tube heat exchange passage thereby permitting selective heating or cooling of the gaseous medium passing through said filter housing.

* * * * *

UNITED STATES PATENT AND TRADEMARK OFFICE
CERTIFICATE OF CORRECTION

PATENT NO. : 4,154,088
DATED : May 15, 1979
INVENTOR(S) : Gert Werner

It is certified that error appears in the above-identified patent and that said Letters Patent are hereby corrected as shown below:

Column 2, line 30, "prevent" should read:

-- present --

Column 8, line 50 (Claim 8, line 4), after "and" add the following:

-- an expansion chamber in communication with the interior of said filter housing and having an outlet from the apparatus for permitting gas from said nozzle to eject through said outlet gas from the interior of said filter housing. --

Signed and Sealed this

Second Day of December 1980

[SEAL]

Attest:

SIDNEY A. DIAMOND

Attesting Officer   Commissioner of Patents and Trademarks